US006235307B1

(12) United States Patent
Huang

(10) Patent No.: US 6,235,307 B1
(45) Date of Patent: May 22, 2001

(54) WATER BASED MEDICATED PLASTER

(75) Inventor: Sam Huang, Tainan (TW)

(73) Assignee: Taiwan Three Mast Pharmaceutical Co., Ltd., Tainan (TW)

( * ) Notice: Subject to any disclaimer, the term of this patent is extended or adjusted under 35 U.S.C. 154(b) by 0 days.

(21) Appl. No.: 09/476,194

(22) Filed: Jan. 3, 2000

(30) Foreign Application Priority Data

Jan. 11, 1999 (TW) ................................ 88200349

(51) Int. Cl.[7] .......................... A61F 13/02; A61F 13/00
(52) U.S. Cl. .................... 424/448; 424/449; 424/443; 602/57; 602/58
(58) Field of Search ........................ 424/448, 449, 424/443; 602/57, 58

(56) References Cited

U.S. PATENT DOCUMENTS 5,415,627 * 5/1995 Rasmussen et al. ............... 602/57
5,476,443 * 12/1995 Cartmell et al. ................... 602/58

* cited by examiner

Primary Examiner—Thurman K. Page
Assistant Examiner—Isis Ghali
(74) Attorney, Agent, or Firm—Rodman & Rodman

(57) ABSTRACT

A medicated plaster includes a fabric base sheet, a medicated composition layer, and a waterproof isolating layer. The base sheet has an upper surface formed with an adhesive layer. The medicated composition layer is disposed above the adhesive layer, and has a medicated composition. The isolating layer is disposed between and is in contact with the adhesive layer and the medicated composition layer so as to prevent the medicated composition from contacting the adhesive layer. The adhesive layer has skin contact portions which are exposed on at least two opposite sides of the isolating layer. The protective layer is disposed on the medicated composition layer for covering the medicated composition layer.

3 Claims, 5 Drawing Sheets

WATER BASED MEDICATED PLASTER

BACKGROUND OF THE INVENTION

1. Field of the Invention

The present invention relates to a medicated plaster, more particularly to a medicated plaster which is convenient to use.

2. Description of the Related Art

Medicated plasters are generally oil-based medicated plasters or water-based medicated plasters. FIG. 1 illustrates a conventional oil-based medicated plaster which includes a base sheet 11 formed from a non-woven fabric, and a layer of medicinal paste 12 applied on the base sheet 11. A cover sheet 13 is provided releasably on the layer of medicinal paste 12 for covering the same. The medicinal paste 12 is typically prepared by mixing a medicinal substance with a rubber, a resin, and an organic solvent. The layer of medicinal paste 12 is relatively sticky, and can be attached firmly to the skin of a person. The cover sheet 13 is made of paper or plastic, such as PET, and is treated with a release agent. The cover sheet 13 prevents different parts of the layer of medicinal paste 12 from sticking together, and prevents dissipation of the medicinal substance. In use, the cover sheet 13 is removed to expose the layer of medicinal paste 12, which is then attached directly on the skin of the person. However, the medicated plaster covers the pores of the skin, and prevents the discharge of sweat from the pores of the skin, thereby resulting in discomfort to the skin of the user. In addition, when the medicated plaster is removed from the skin, it is likely that hairs on the skin of the user are removed together with the medicated plaster. Therefore, the oil-based medicated plaster unavoidably causes discomfort and pain to the user during use.

Referring to FIG. 2, a conventional water-based medicated plaster includes a medicated piece 15 and an adhesive piece 14. The adhesive piece 14 includes a base sheet 141 made of a non-woven fabric and applied with an adhesive layer 142, and a cover sheet 144 having a release surface 143 facing the adhesive layer 142 and treated with a release agent. Prior to use of the medicated plaster, the cover sheet 144 is laid on the adhesive layer 142 for covering the same, as shown by the phantom lines in FIG. 2. The medicated piece 15 includes a support layer 151 formed of a non-woven fabric, a medicated composition layer 152 applied on the support layer 151, and a waterproof protective layer 153 disposed on the medicated composition layer 152 for covering the same. In order to prevent the medicated composition in the medicated composition layer 152 from permeating into the adhesive layer 142 to undesirably decrease the adhesive strength of the adhesive layer 142, the medicated piece 15 and the adhesive piece 14 are packed separately in different inner bags, which are then received in an outer bag. In use, the inner and outer bags are each opened to permit joining of the medicated piece 15 to the adhesive piece 14 by removing the cover sheet 144 from the adhesive piece 14 to expose the adhesive layer 142, and attaching the support layer 151 of the medicated piece 15 to the adhesive layer 142. The adhesive layer 142 has a size larger than that of the medicated piece 15 such that the medicated piece 15 can be adhered to a central portion of the adhesive layer 142 to expose a peripheral portion of the adhesive layer 142 around the medicated piece 15. Finally, the protective layer 153 is removed to permit attachment of the medicated plaster to the skin of the user. The water-based medicated plaster is found to be more comfortable to the skin of the user. However, as the joining of the medicated piece 15 to the adhesive piece 14 involves complicated procedures, the conventional water-based medicated plaster of FIG. 2 is not convenient to use, especially for an old person or a person who is injured at certain body parts. Therefore, the conventional medicated plasters of FIGS. 1 and 2 are not satisfactory.

SUMMARY OF THE INVENTION

The object of the present invention is to provide a medicated plaster which is convenient to use and which does not cause discomfort to the skin of a user.

Accordingly, the medicated plaster of the present invention includes a fabric base sheet, a medicated composition layer, a waterproof isolating layer, and a waterproof protective layer. The base sheet has an upper surface formed with an adhesive layer. The medicated composition layer is disposed above the adhesive layer, and has a medicated composition. The isolating layer is disposed between and is in contact with the adhesive layer and the medicated composition layer so as to prevent the medicated composition from contacting the adhesive layer. The adhesive layer has skin contact portions which are exposed on at least two opposite sides of the isolating layer. The protective layer is disposed on the medicated composition layer for covering the medicated composition layer.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
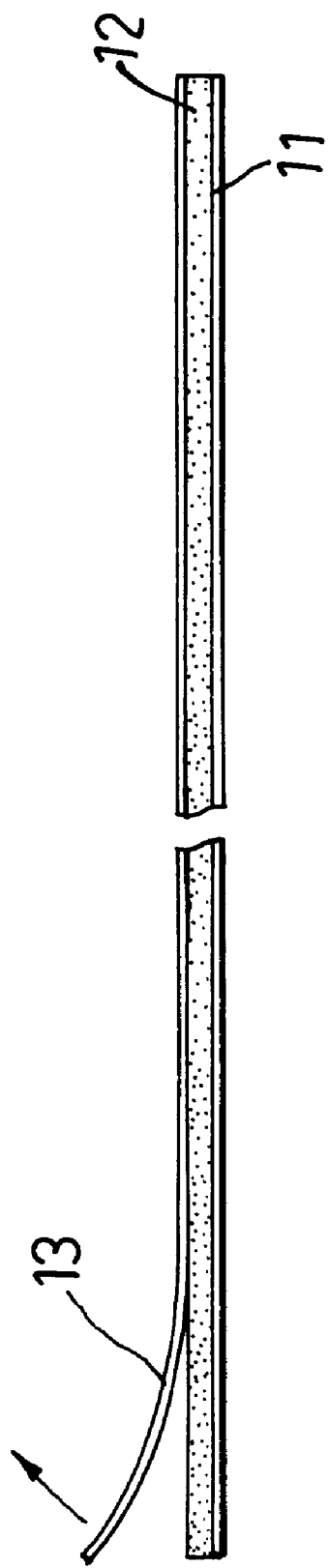
FIG. 1 is a cross-sectional view of a conventional oil-based medicated plaster.
Figure 2:
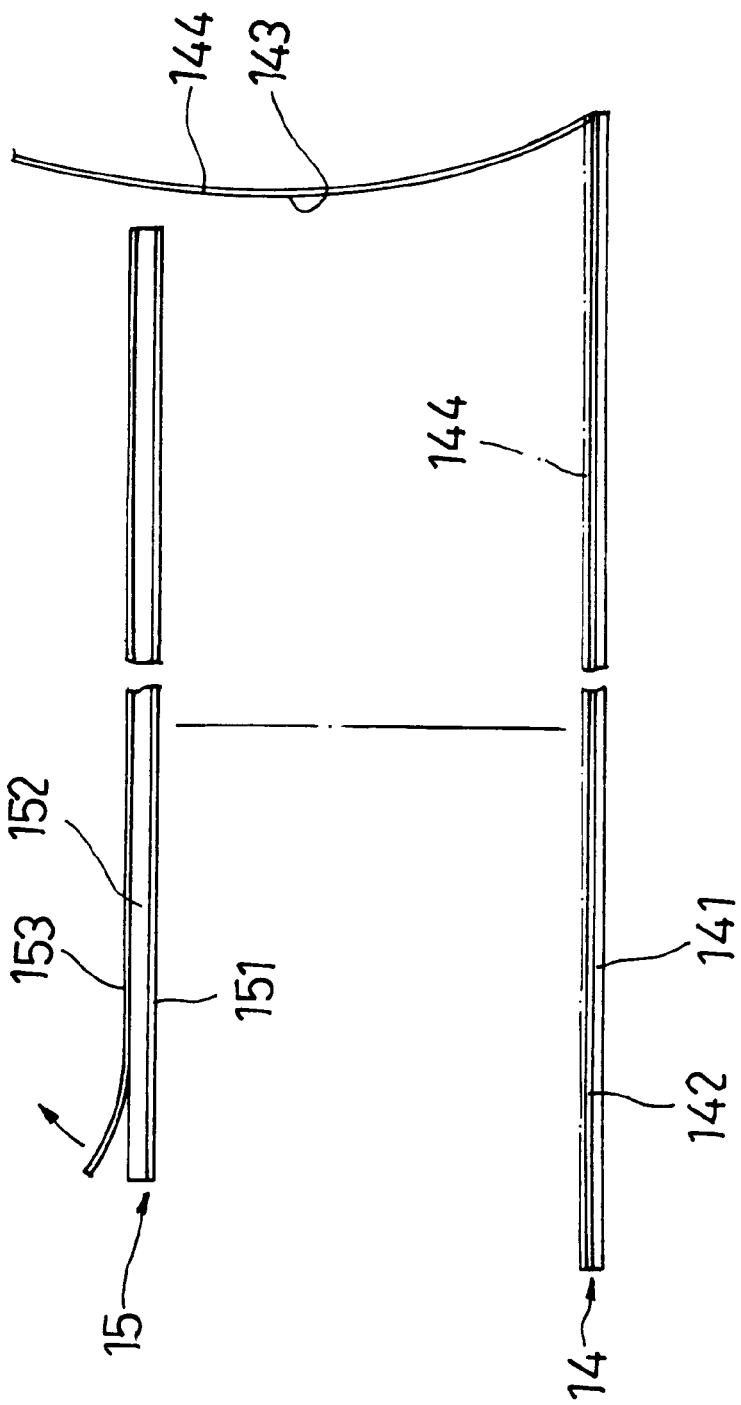
FIG. 2 is a schematic view of a conventional water-based medicated plaster.
Figure 3:
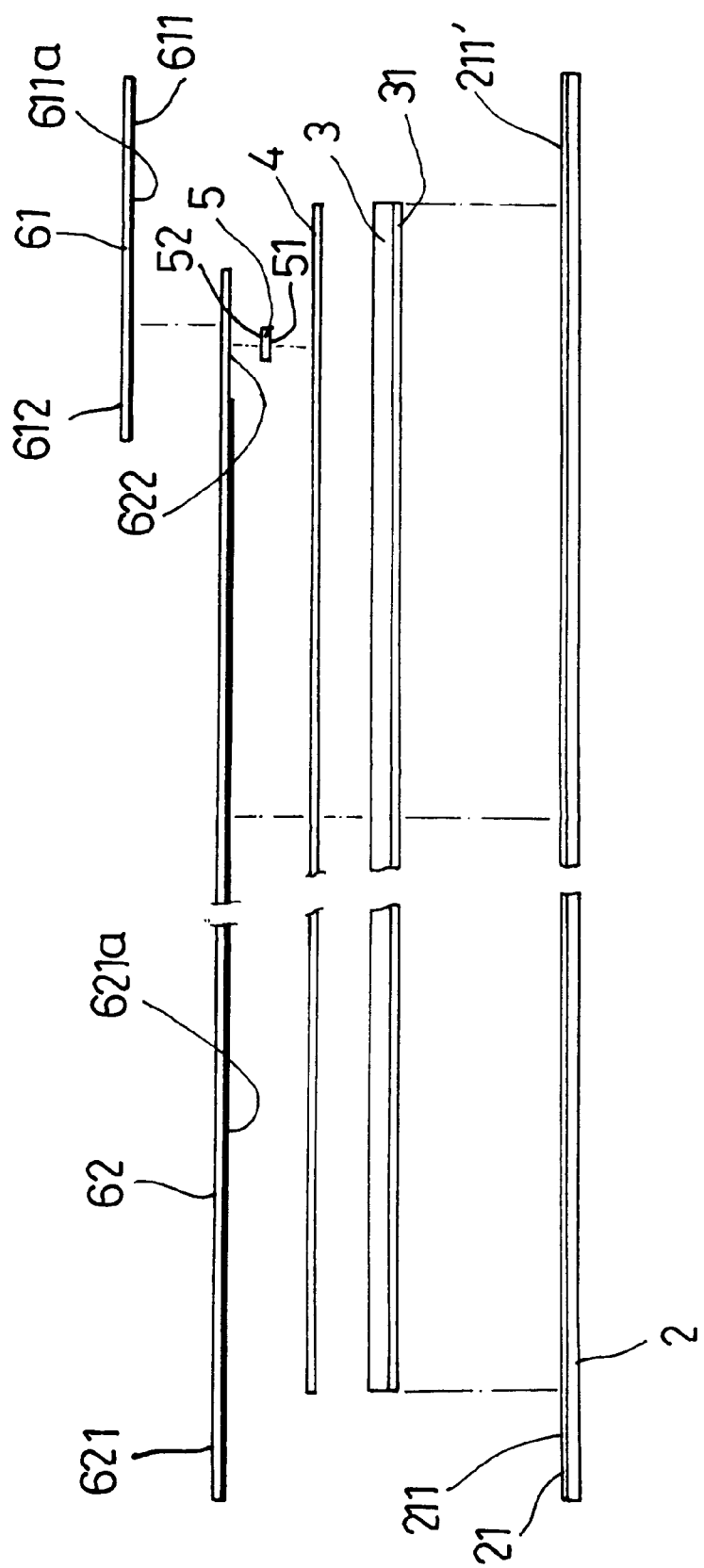
FIG. 3 is an exploded schematic view of a preferred embodiment of the medicated plaster of the present invention.
Figure 4:
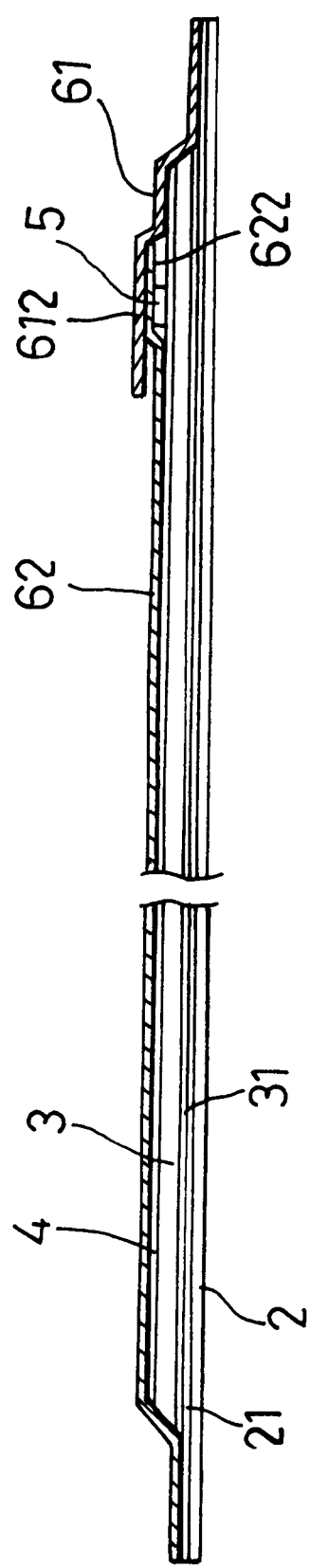
FIG. 4 is a partly sectional, schematic view of the preferred embodiment when assembled.

Referring to FIGS. 3 and 4, the preferred embodiment of the medicated plaster of the present invention is shown to include a base sheet 2, a medicated composition layer 3, a waterproof isolating layer 31, a waterproof protective layer 4, a connecting strip 5, and lower and upper cover sheets 62, 61.

The base sheet 2 is made of a non-woven fabric, and has an upper surface formed with an adhesive layer 21.

The medicated composition layer 3 has a water-based medicated composition, and is disposed above the adhesive layer 21. The isolating layer 31 is disposed between and is in contact with the adhesive layer 21 and the medicated composition layer 3, and is adhered to the adhesive layer 21. The isolating layer 31 has a size not smaller than that of the medicated composition layer 3 so as to prevent the medicated composition layer 3 from contacting the adhesive layer 21, thereby preventing the medicated composition from permeating into the adhesive layer 21 to avoid undesirable reduction in the adhesive strength of the adhesive layer 21. In the present embodiment, the size of the isolating layer 31 is substantially identical to that of the medicated composition layer 3, and is smaller than that of the adhesive layer 21 such that the adhesive layer 21 has opposite skin contact portions 211, 211' that are exposed on at least two opposite sides of the isolating layer 31. In the present embodiment, the skin contact portions 211, 211' are exposed around the isolating layer 31 and the medicated composition layer 3.

The protective layer 4 is made of a plastic material such as polypropylene, and is disposed on top of the medicated composition layer 3. The protective layer 4 has a size equal to or greater than that of the medicated composition layer 3 for covering the same so as to prevent evaporation and dissipation of moisture and the medicated composition that are contained in the medicated composition layer 3. In the present embodiment, the size of the protective layer 4 is substantially identical to that of the medicated composition layer 3.

The lower cover sheet 62 is disposed above the protective layer 4, and has opposite first and second end portions 621, 622. The first end portion 621 has a lower surface which is applied with a release agent to form a release layer 621a on the lower surface. The second end portion 622 has a lower surface free of a release agent. The first end portion 621 of the lower cover sheet 62 is disposed on one of the skin contact portions 211 of the adhesive layer 21 for covering the skin contact portion 211. The connecting strip 5 is disposed between the protective layer 4 and the second end portion 622 of the lower cover sheet 62, and is adjacent to an edge portion of the protective layer 4 for connecting adhesively the second end portion 622 of the lower cover sheet 62 to the protective layer 4 so as to permit removal of the protective layer 4 from the medicated composition layer 3 together with the lower cover sheet 62. In the present embodiment, the connecting strip 5 has an adhesive lower surface 51 adhered to an upper surface of the protective layer 4, and an adhesive upper surface 52 adhered to the lower surface of the second end portion 622 of the lower cover sheet 62.

The upper cover sheet 61 has a first end portion 611 with a lower surface which is applied with a release agent to form a release layer 611a, and a second end portion 612 opposite to the first end portion 611. The first end portion 611 of the upper cover sheet 61 is disposed on another one of the skin contact portions 211' for covering the skin contact portion 211'. The second end portion 612 of the upper cover sheet 61 is disposed on the second end portion 622 of the lower cover sheet 62, and overlaps the second end portion 622 of the lower cover sheet 62. The upper and lower cover sheets 61, 62 are laid on the skin contact portions 211, 211' and the protective layer 4 as a covering.

With the provision of the isolating layer 31 to isolate the medicated composition layer 3 from the adhesive layer 21, the medicated plaster of the present invention can be packed within a single bag, without the need for several bags to receive the medicated composition layer and the adhesive layer separately, as taught in the prior art.

Figure 5:
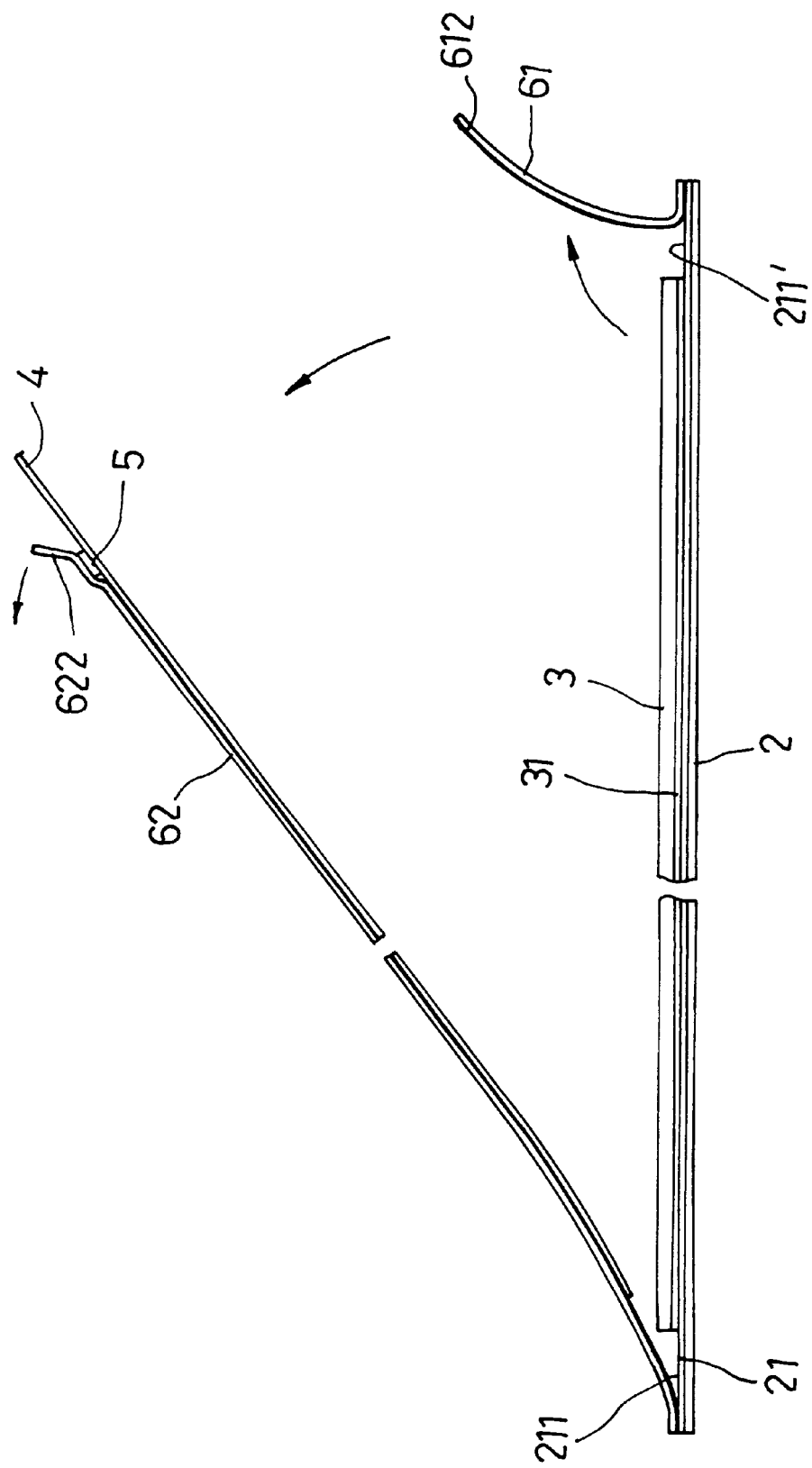
FIG. 5 is a schematic view illustrating the preferred embodiment when in a state for use.

Referring to FIG. 5, in use, the upper and lower cover sheets 61, 62 are lifted at the overlapping second end portions 612, 622 for removing the upper and lower cover sheets 61, 62 so as to expose the skin contact portions 211, 211'. Since the protective layer 4 is connected to the lower cover sheet 62 by virtue of the connecting strip 5, the protective layer 4 is removed at this time together with the lower cover sheet 62 to expose the medicated composition layer 3. The medicated plaster can thus be attached to the skin of the user by virtue of the skin contact portions 211, 211' of the adhesive layer 21 around the medicated composition layer 3. Therefore, the medicated composition layer 3 and the skin contact portions 211, 211' of the adhesive layer 21 can be exposed by simply removing the upper and lower cover sheets 61, 62, which results in simultaneous removal of the protective layer 4. The medicated plaster of the present embodiment is thus convenient to use by older persons or persons who are injured at certain body parts.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. A water based medicated plaster comprising:

a non-woven fabric base sheet having an upper surface formed with an adhesive layer;

a water based medicated composition layer disposed above said adhesive layer;

a waterproof isolating layer formed of polypropylene having an area at least as large as the area of the medicated composition layer and being disposed between and in contact with said adhesive layer and said medicated composition layer so as to prevent said medicated composition layer from contacting said adhesive layer, said waterproof isolating layer having an area smaller than that of said adhesive layer so that said adhesive layer has skin contact portions exposed on at least two opposite sides of said waterproof isolating layer;

a waterproof protective layer formed of polypropylene disposed on top of said medicated composition layer for covering said medicated composition layer;

a lower cover sheet having a first end portion which has a lower surface formed with a layer of release agent, and a second end portion opposite to said first end portion, said first end portion being disposed on one of said skin contact portions of said adhesive layer for covering said one of said skin contact portions, said second end portion being connected to said waterproof protective layer so as to permit removal of said waterproof protective layer from said water based medicated composition layer together with said lower cover sheet; and an upper cover sheet having a first end portion with a lower surface which is provided with a layer of release agent and which is disposed on another one of said skin contact portions of said adhesive layer for covering said another one of said skin contact portions, said upper cover sheet further having a second end portion which is opposite to said first end portion of said upper cover sheet and which overlaps said second end portion of said lower cover sheet.

2. The water based medicated plaster according to claim 1, wherein said skin contact portions are exposed around said isolating layer and said water based medicated composition layer.

3. The water based medicated plaster according to claim 2, further comprising a connecting strip disposed between said waterproof protective layer and said second end portion of said lower cover sheet, said connecting strip having an adhesive upper surface adhered to said second end portion of said lower cover sheet and an adhesive lower surface adhered to said waterproof protective layer for connecting said lower cover sheet to said waterproof protective layer.

* * * * *